United States Patent [19]

Yamada et al.

[11] Patent Number: 5,911,713
[45] Date of Patent: Jun. 15, 1999

[54] ABSORBENT PRODUCT WITH LEG CLOSURES

[76] Inventors: Jiro Yamada; Eiro Fukuda, both of c/o Procter & Gamble Far East, Inc., 17, Koyo-cho Naka 1-chome, Higashianda-ku, Kobe 658, Japan

[21] Appl. No.: 08/793,222
[22] PCT Filed: Aug. 15, 1995
[86] PCT No.: PCT/US95/10359
  § 371 Date: Feb. 19, 1997
  § 102(e) Date: Feb. 19, 1997
[87] PCT Pub. No.: WO96/05792
  PCT Pub. Date: Feb. 29, 1996

[30] Foreign Application Priority Data

Aug. 23, 1994 [JP] Japan .................................. 6-198769

[51] Int. Cl.⁶ ..................................................... A61F 13/15
[52] U.S. Cl. ........................ 604/385.2; 604/393; 604/396
[58] Field of Search .................................. 604/385.2–397

[56] References Cited

U.S. PATENT DOCUMENTS 4,816,025  3/1989  Foreman .............................. 604/385.2

FOREIGN PATENT DOCUMENTS 2253131  2/1992  United Kingdom .................. 604/393

*Primary Examiner*—Robert A. Clarke
*Attorney, Agent, or Firm*—Theodore P. Cummings; Jeffrey V. Bamber; Jacobus C. Rasser

[57] ABSTRACT

Stretchable leg cuffs are put around the legs of a wearer with little gap therebetween, whereby liquid leakage around the legs can be substantially prevented. Elastic bodies are extended on side flaps formed of a backsheet along lengths of the side flaps. Stretchable leg cuffs for encircling the legs of a wearer extend outwardly from the side edges of the side flaps along the lengths of the side flaps.

4 Claims, 5 Drawing Sheets

ABSORBENT PRODUCT WITH LEG CLOSURES

BACKGROUND OF THE INVENTION

The present invention relates to an absorbent article having a leg closure which dynamically fits comfortably to the legs of wearer, preventing without failure liquid leakage about the legs.

Absorbent articles with leg closures which are used in direct or indirect contact with wearers to absorb and contain body exudates of the wearers are exemplified by diapers, incontinent briefs, pull-on diapers, diapers, diaper holders, etc.

The major function of the absorbent articles with leg closures, such as disposable diapers and incontinent briefs or undergarments is to absorb body exudates of wearers by the absorbent cores, and prevent the body exudates contained in the absorbent cores from soiling, wetting or otherwise contaminating clothing of the wearers or other articles, such as bedding, that come in contact with the wearers.

Commonly used disposable diapers comprise an absorbent body including a topsheet, backsheet and an absorbent core, and non-elastic side flaps each generally including a non- elastic topsheet, a non-elastic backsheet provided adjacent the longitudinal edges of the diaper. Elasticized side flaps are effective to present a liquid impervious barrier between the edges of the diaper and the contacting clothing, and in addition, provide a gasketing action about the legs of the wearer to maintain a seal about the legs and minimizing gapping. One type of the non-elastic side flaps has elasticized bands to be elasticized around the legs of a wearer.

Pull-on diapers, such as training pants have become popular, especially for use on toilet-training children. Some conventional training pants have the waist opening and the leg openings at least partially encircled with stretch- able bands so that the waist opening and the leg openings are elasticized.

In another type of pull-on diapers, discrete stretchable members are attached to the edges of the side flaps in the front waist area and the rear waist area so that the waist opening is elasticized. Stretchable side panels are effective to from a pull-on diaper, but it has been found that the wide stretchable side panels are preferable to sustain wide range dynamic fit.

In the latter of the above-described absorbent articles, it has been necessary that the stretchable side panels are attached to the edges of the side flaps, or the stretchable side panels are associated with the side flaps. To this end, a width of such stretchable side panels and a width of the plasticized side flap must be balanced with each other in order to provide an appropriate waist fit range in the waist opening and an effective gasketing action about leg openings.

But contradictorily for a large width (a substantially stretchable part except an allowance for attachment) of the stretchable side panel, a sufficient width f the side flap to produce a sufficient gasketing action while for a large width of the side panel, a sufficient width of the stretchable side panel to produce sufficient dynamic fit cannot be allowed. Accordingly there has been a barrier to maximizing the functions of the stretchable side panels and the side flaps by maximizing balanced widths of the stretchable side panels and the side flaps.

SUMMARY OF THE INVENTION

The present invention was made in view of the above-described problem. An object of the present invention is to provide an absorbent article with a leg closure which secures wide dynamic fit around a waist and can prevent liquid from leaking around the legs.

The absorbent product with leg closures according to the present invention comprises an absorbent body including an absorbent core between a topsheet and a backsheet and arranged to cover at least the crotch of a wearer; a pair of side flaps extended widthwise from the absorbent core and formed of the backsheet; elastic bodies arranged on the respective side flaps along lengths of the side flaps and elasticizing the side flaps; a pair of stretchable side panels extended outward from side edges of lengthwise ends of the side flaps; stand-up barrier cuffs provided on a side of the absorbent body near to the topsheet of the absorbent body; barrier cuffs extended on the topsheet inner of the side flaps along a length of the absorbent body; and stretchable leg cuffs extended further outward from side edges of the side flaps along the lengths of the side flaps for enclosing the lengths of the wearer.

In the absorbent product with leg closures according to the present invention, the side flaps provided on the sides of the absorbent body, and e stretchable leg cuffs provided outward on the side edges of the side flaps are put tightly around the legs of a wearer over a wide width, whereby penetration and leakage of liquid from the wet absorbent product into garments contacting the edge of the absorbent product can be prevented without failure. It is not necessary to form the side flaps wide, and the stretchable side panels attached to the side flaps can have an effective width. Dynamic fit can be secured wide around the waist.

As described above, according to the present invention, the elastic bodies provided in the side flaps, and the stretchable leg cuffs elastically fit the vicinities of the leg openings of the absorbent product to the legs of a wearer. The elastic leg cuffs are arranged around the legs of a wearer with little gas around the legs to prevent liquid leakage around the legs. Furthermore, the stretchable leg cuffs are hindered from being bent inside. Even when body exudates are held by the absorbent body, the absorbent body is retained at the crotch. The side panels are attached tot he side flaps, so that a width of the side panels can be set independently of a width of the stretchable leg cuffs, and dynamic fit can be secured around a waist.

DETAILED DESCRIPTION OF THE PREFERRED EMBODIMENTS

Figure 1:
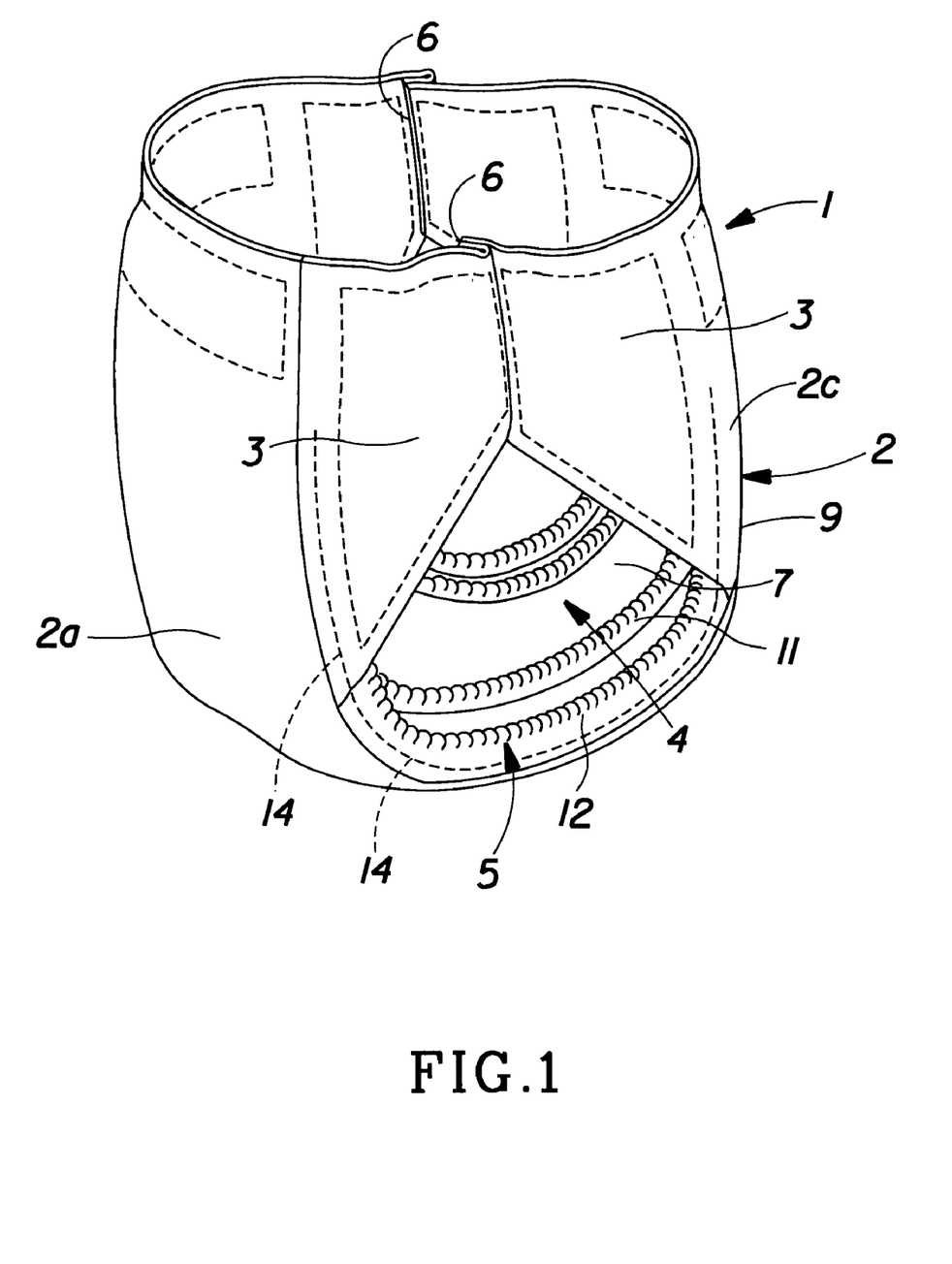
FIG. 1 is a perspective view of an example of the absorbent article with the leg closures applied to a disposable pull-on diaper.
Figure 2:
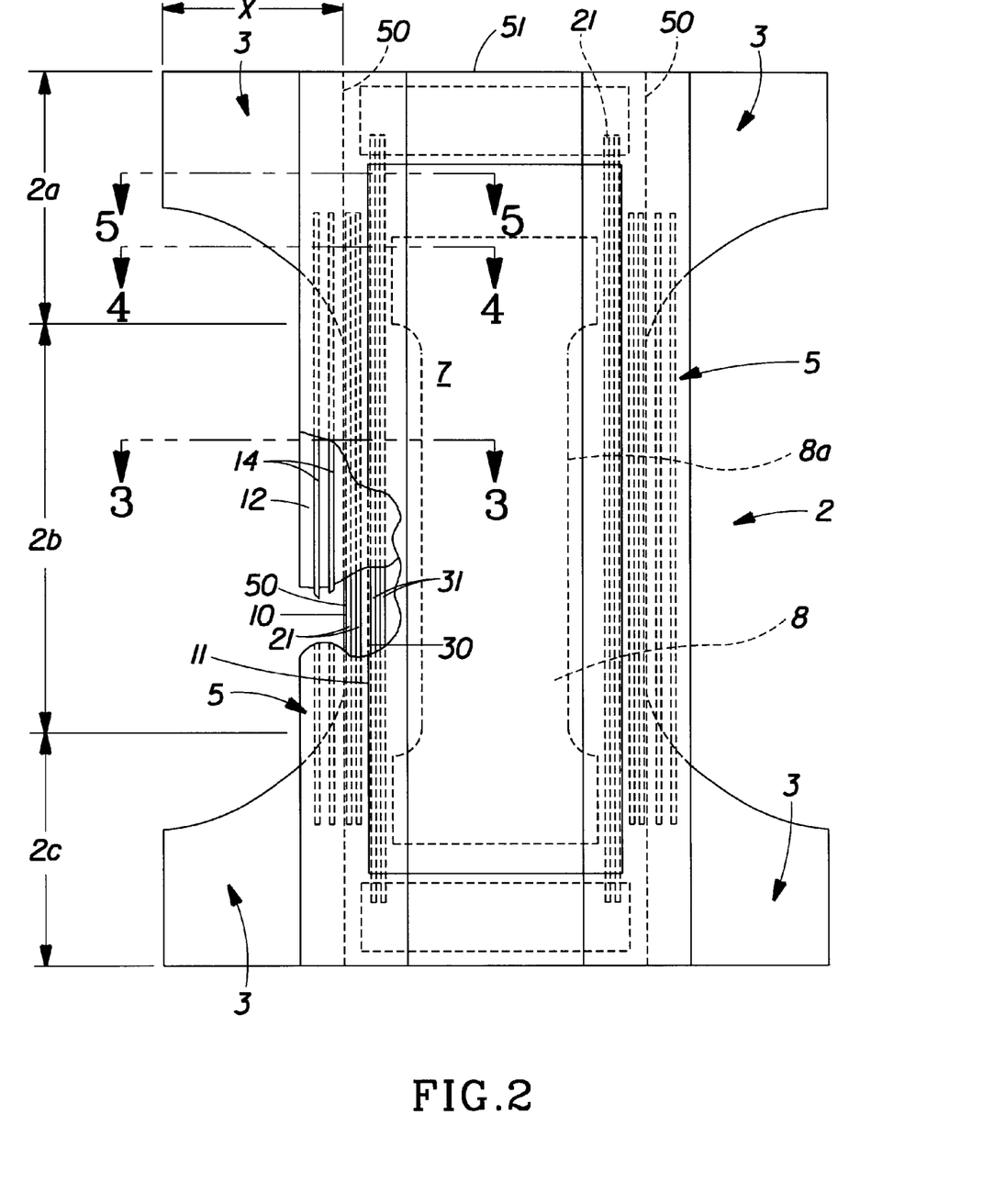
FIG. 2 is a development view of the partially broken disposable pull-on diaper of FIG. 1.

There will be explained preferred embodiments of the present invention with reference to the drawings attached hereto. FIG. 1 is a view of a disposable pull-on diaper to which the absorbent article according to the present invention is applied. FIG. 2 is a partially broken view of the disposable pull-on diaper of FIG. 1 before a front portion 2a of the disposable pull-on diaper and a rear portion 2c thereof are jointed by side seams 6. The disposable pull-on diaper 1 of FIG. 1 comprises an absorbent chassis 2 including the front portion 2a, a crotch portion 2b and a rear portion 2c and generally has a rectangular shape, an hour-glass shape, a T-shape, a asymmetric, preferably symmetrical modified hour-glass shape, a pair of stretchable side panels 3, 3 extended outward from the front portion 2a of the absorbent chassis 2 and the rear portion 2c thereof, and side beams 6 formed by, e.g., heat seal means and respectively joining those of the stretchable side panels 3, 3 extended in the same sides.

Figure 3:
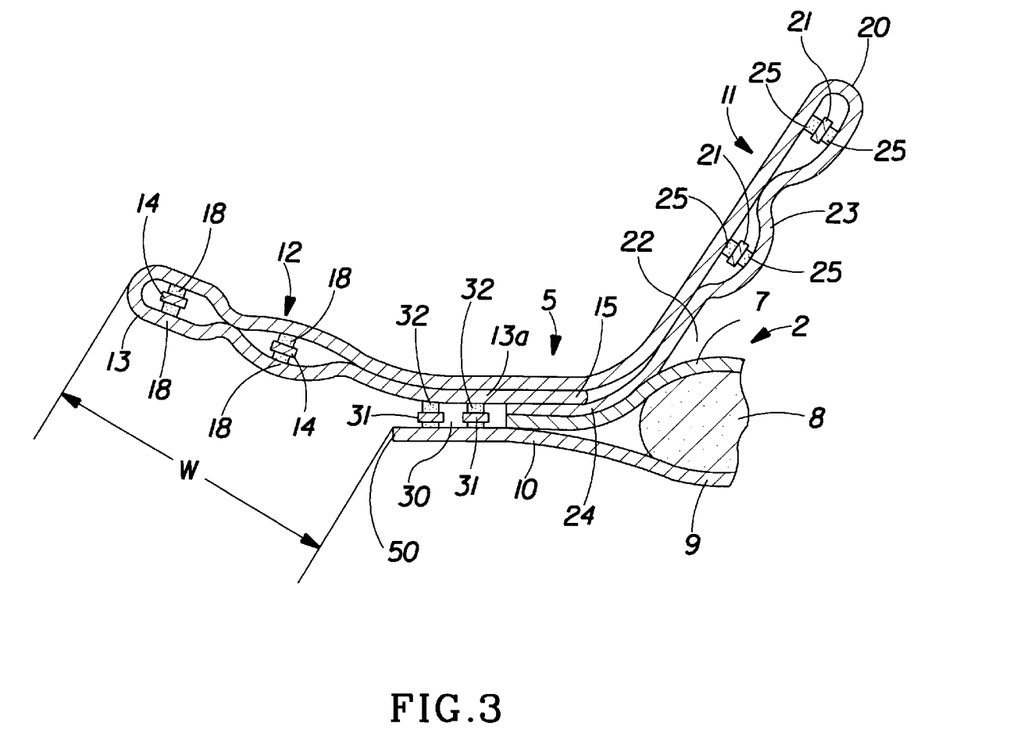
FIG. 3 is a sectional view along the line 3—3 in FIG. 2.

As shown in FIG. 3, the absorbent chassis 2 includes a liquid pervious topsheet 7, an absorbent core 8 and a liquid impervious backsheet 9. The top sheet 7 and the backsheet 9 have generally larger lengths and widths than the absorbent core 8 and extended outward beyond the edge 8a of the absorbent core 8. The extended portions of the backsheet 9 and the top sheet 7 constitute side flaps 10 at least at the crotch portion 2b. Elastic members 30 are provided on the backsheet 9 of the side flaps 10 extended outward beyond the topsheet 7 of the side flap 10 to elasticize the side flaps 10.

The absorbent core 8 is comfortably non-irritating to the skin of a wearer, and has a function of absorbing and retaining liquids, such ac urine and other body exudates, and is generally made of the so-called airfelt, which is comminuted wood pulp. The absorbent core 8 may be made of other suitable materials, such as creped cellulose wadding, meltblown polymers including conform, chemically stiffened, modified or crosslinked cellulose fibers, tissue including tissue wraps and tissue laminates, absorbent foams, absorbent sponges, super-absorbent polymers, absorbent gelling materials or any equivalent materials, or their combinations. The configuration and construction of the absorbent core 8 can be varied as required, but total absorption capacities of the absorbent core 8 must correspond to design loads as diapers and intended applications. The size and absorption capacity of the absorbent core 8 is varied in accordance with wearers from babies to adults.

The backsheet 9 is liquid impervious (e.g., to urine), and preferably is made of thin plastic film. The backsheet 9 is positioned adjacent the garment side of the absorbent core 8, and is adhered to the absorbent core 8 by known attachment means (not shown), e.g., by a uniform continuous layer of an adhesive, a patterned layer of an adhesive, or an array of separate lines, spirals or spots of an adhesive.

The backsheet 9 prevents body exudates absorbed and retained in the absorbent core 8 from wetting articles in contact with the diaper, e.g., bed sheets, underwears. Accordingly the backsheet 9 can be made of worn fabric, nonwoven fabric, polymer film, such as thermoplastic film of polyethylene, polypropylene, etc., a composite material of, e.g., nonwoven fabric covered with film. Preferably the backhseet 9 is a thermoplastic film of an bout 0.012–about 0.051 mm thickness. It is preferred that the backsheet 9 is embossed and/or matte finished so that the backsheet 9 has a fabric-like appearance. It is also preferable that the backsheet 9 is made of a material which can not only prevent pass of body exudates, but also permits water vapour to escape from the absorbent core 8.

The topsheet 7 is made of, e.g., porous foams, reticulated foams, aperture plastic films o woven or non woven webs of natural fibers (e.g., wood or cotton fibers), synthetic fibers (e.g., polyester or polypropylene fibers), or a woven or nonwoven fabrics of natural fibers and synthetic fibers). Preferably, the topsheet 7 is made of a hydrophobic material to isolate the wearer's skin from liquids contained in the absorbent core 8. The topsheet 7 is positioned adjacent the body surface of the absorbent core 8 and is joined to the absorbent core 8 and the backsheet 9 by known attachment means (not shown). The top sheet 7 is compliant, soft feeling, non-irritating to the wearer's skin, and pervious to liquid (e.g., urine). The top sheet 7 is suitably made of nonwoven fabric webs of spunbonded carded or wet laid fibers. Preferably the topsheet 7 is made of webs of polypropylene fiber staples carded by a carding machine and then thermally bonded.

The leg cuffs 5 are made of a flexible material which easily conforms to a configuration and outline of a wearer and is made of various material, such as polypropylene, polyester, rayon, nylon, foam, plastic films, formed films, elastic laminates or elastic foams. The leg cuffs 5 can be formed by various techniques. For example, the leg cuffs 5 may be made of woven fabric, nonwoven fabric, spunbonded web, carded web of polypropylene adhered to liquid impervious polyethylene film.

Each of the leg cuffs 5 comprises a stand-up barrier cuff 11 and an stretchable leg cuff 12. The stand-up barrier cuffs 11 provide a structure to hold and contain body exudates within the diaper 1. The stretchable leg cuffs 12 dynamically fit the legs of a wearer to prevent free flow of body exudates overflowing the stand-up barrier cuffs and confine and hold the body exudates in the diaper I and to generate gasket function around the legs of the wearer.

As shown in FIG. 3, the stretchable leg cuffs 12 includes folded-back portions 13. One or a plurality of elastic members 14 (two in FIG. 3) are arranged on each folded-back portion 13. The stretchable leg cuffs 12 are so arranged that the folded-back portions 13 are positioned on the outside side remote from the side flaps 10 and inner ends 15 are positioned on the upper side of the top sheet 7. The folded-back portions 13 of the stretchable leg cuffs 12 and the inner ends 15 are spaced from each other to determine an effective width of the stretchable leg cuffs 12. The folded- back portions 13 and the inner ends 15 are spaced from each other preferably linearly and parallelly, or non-parallelly and linearly or curved. The stretchable leg cuffs 12 are of circular, square, rectangular or other section. An effective width of the stretchable leg cuffs 12 is a parameter for decreasing leakage of body exudates from the diaper.

The effective width of the stretchable leg cuffs 12 is a width from the outer edges 50 of the side flaps 10 to the forward end of the stretchable leg cuffs 12 extended outward from the side edges 50 of the side flaps 10, and is shown as a width W in FIG. 3. It is preferable that the diaper for children has the effective width W of 2.5 –50 mm and more preferably 5 –35 mm. When the stretchable leg cuffs 12 have an effective width of below 2.5 mm, gaps are formed between the legs of a wearer and the folded-back portions 13, and sometimes body exudates overflow the folded-back portions 13 to the outer edge of the diaper 1. When the stretchable leg cuffs 12 have an effective width W of above 50 mm, the leg openings 4 cannot be sufficient, and the diaper is difficult to put on. When the diaper is for adults, the stretchable leg cuffs 12 have preferably an effective width W of 4–90 mm, ore preferably 8–50 mm.

It is preferable that the folded-back portions 13 of the stretchable leg cuffs 12 are not fixed to the side of the diaper at least at the crotch portion so as to be spaced from the side flaps 10. The folded-back portions 13 are spaced from the side flaps 10 so that the stretchable leg cuffs 12 can be readily brought into contact with a wearer and secured at the crotch portion, tightly fit to the hips of the wearer.

It is preferable that the folded-back portions of the stretchable leg cuffs 12 are positioned outside of the inner ends 15 in the front portion 2a of the diaper 1 and the rear portion 2c thereof so that formation of a gap between the folded-back portions 13 of the stretchable leg cuffs 12 and the legs of a wearer is prevented, effective barriers for flow of body exudates being made. Preferably the folded-back portions 13 are fixed to the side panels 3 in the front portion 2a of the diaper and in the rear portion 2c thereof, so that the folded-back portions 13 are not reversed. But in the case that the stretchable leg cuffs 12 are made of, e.g., nonwoven fabric or others, when the folded-back portions 13 are fixed to the side panels 3, the fixed parts cannot stretch in the stretching direction of the side panels 3. Consequently a stretch width of the side panels 3 are adversely reduced.

Figure 7:
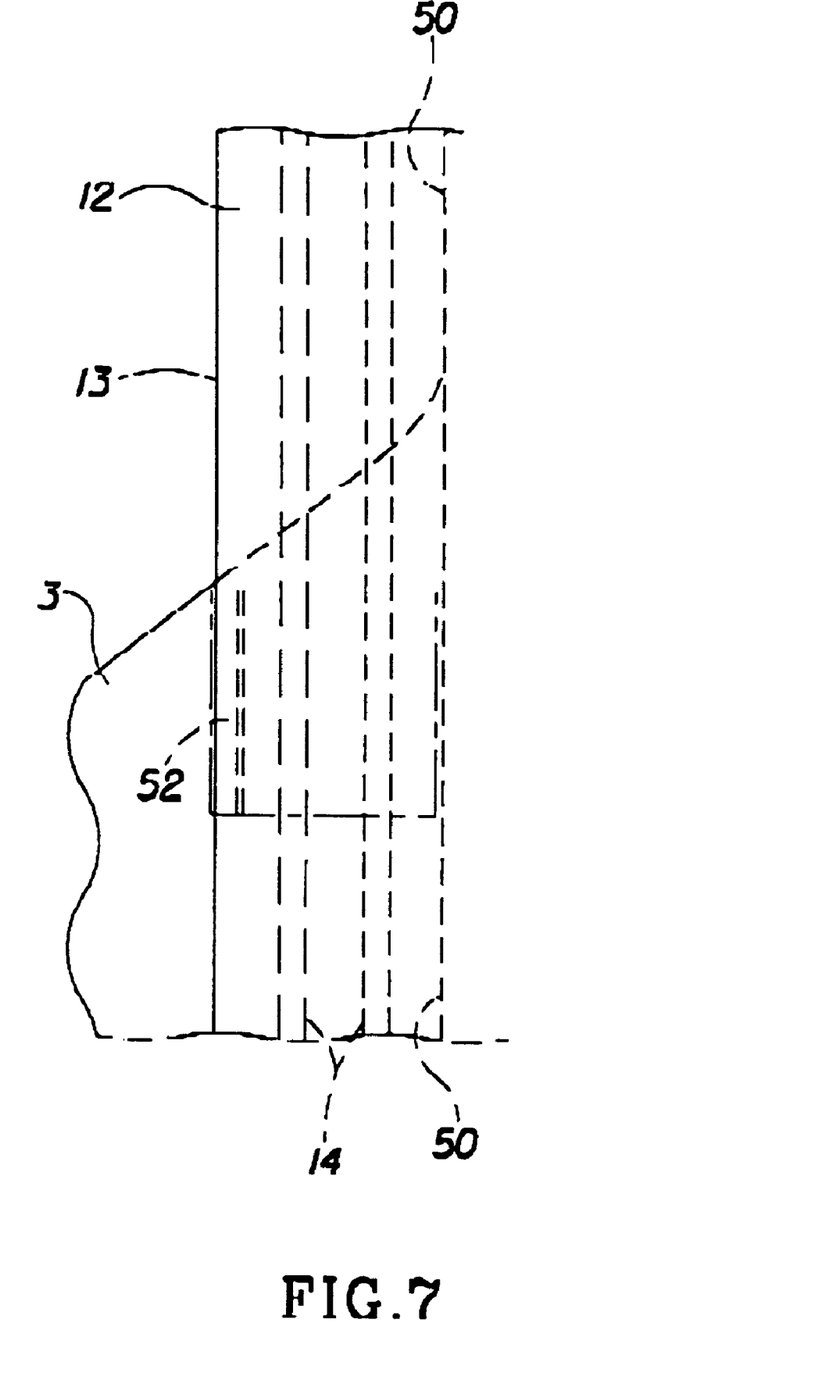
FIG. 7 is an enlarged view of the side panel in FIG. 2.

Then, as shown in FIG. 7, fixed portions 52 are partially provided in parallel with the folded-back portions 13 to fix the stretchable leg cuffs 12 to the side panels 13. Fixing means for the fixation is arbitrary know fixing means, such as ultrasonic bonding, pressure sensitive/heat bonding, seal using a bonding pattern, or an adhesive, preferably adhesive beads of a hot melt adhesive. After the side panels 3 and the stretchable leg cuffs 12 are thus fixed partially to each other in parallel with the folded-back portions 13, t least the region indicated by the one-dot chain line in FIG. 7 is elasticized. The stretchable leg cuffs 12 in this region are made stretchable in the same direction as the side panels 3. The side panels 3 can thus have a sufficient stretch width. As an elasticization method, the elasticization using known ring rolls is applicable.

Figure 4:
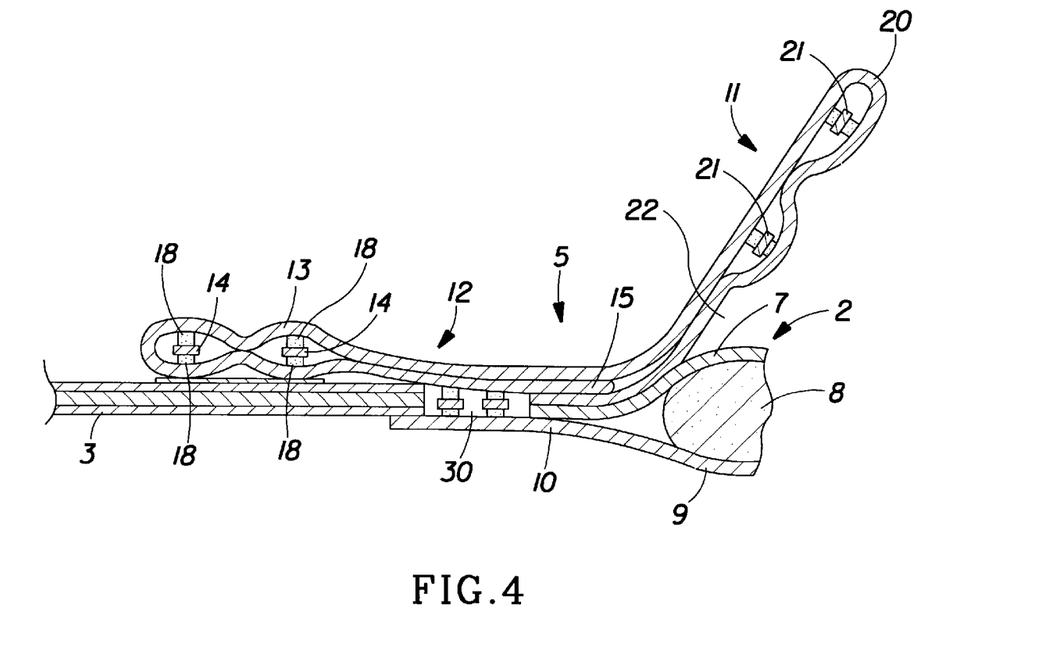
FIG. 4 is a sectional view along the line 4—4 in FIG. 2.

As shown in FIGS. 2 and 4, the ends of the folded-back portions 13 of the stretchable leg cuffs are parallel with each other and parallel with a length of the diaper in the front and the rear portions 2a, 2c of the diaper 1. This is a preferable embodiment. But the ends of the folded-back portions may be slanted toward each other. Especially in a case that the stretchable leg cuffs 12 are made of a material of low extensibility, the ends of the folded-back portions 13 can be arranged slant toward each other.

In the diaper 1 of FIG. 1 the stretchable leg cuffs 12 are joined to the respective side flaps 10. Here "joined" includes any means for securing the stretchable leg cuffs 12 to the diaper, and includes embodiments where the stretchable leg cuffs 12 are separate members directly or indirectly secured to the side flaps 10 or embodiments wherein the stretchable leg cuffs 12 are made of the same members or material as the stand-up barrier cuffs 11/ The stretchable leg cuffs 12 may be joined to the backsheet 9, the top sheet 7 or combination of other elements. In the preferred embodiment, the stretchable leg cuffs 12 are joined to the side flaps 10 (parts of the topsheet 7 and of the backsheet ) forming the side flaps 10 by seal means, such as an adhesive. It is preferred that the stretchable leg cuffs 12 are made of the same material as the stand-up barrier cuffs 11. The material is hydrophobic polypropylene carded nonwoven.

One or a plurality of elastic members 14 are provided on the folded-back portions 13 of the stretchable leg cuffs 12 so as to elasticize the stretchable leg cuffs 12. The elastic members 14 pace the edges of the folded-back portions 13 from the side flaps 10 and rises the stretchable leg cuffs 12 to facilitate application of the diaper to a wearer and to provide gasket action around the buttocks of the wearer to fit the stretchable leg cuffs 12 thereto. The elastic members 14 are secured to the stretchable leg cuffs 12 elastically stretched and, in their normal free state, contract or gather the folded-back portions 13 of the stretchable leg cuffs 12. A length of the elastic members 14 are generally determined in accordance with a design. The elastic members 14 are extended in the crotch portion 2b along substantially entire lengths of the stretchable leg cuffs 12 as shown in FIG. 2, but may have other lengths.

As shown in FIGS. 2 and 3, the elastic members 14 are fixed in the folded-back portions 13 by elastic attachment means 18. The elastic attachment means 18 is flexible and has adhesion which allows the elastic members 14 to be held extended. The elastic members 14 may have only the ends secured to the stretchable leg cuffs 12, but preferably are secured to the stretchable leg cuffs 12 along their entire lengths. The elastic attachment means 18 is, e.g., adhesive beads of a hot melt adhesive. The elastic members 14 are secured to the stretchable leg cuffs 12 by ultrasonic bonding or pressure sensitive/heat seal, and can be bonded simply with an adhesive. The elastic members 14 are preferably formed of natural rubber strips of a 0.18 mm×1.5 mm sectional area. Other preferable elastic members 14 are as of elastomer film, polyurethane film, Lycra, elastic foam and foamed elastic scrim. In the preferred embodiment, the elastic members 14 and the elastic attachment means 18 are 0.013 mm-thickness extended strips of an adhesive.

The elastic members 14 can have various shapes. For example, the elastic members 14 can have various widths. The elastic members 14 may be a single strand of an elastic material or a plurality of parallel or unparallel strands thereof, or may be linear or curved.

The means for spacing the folded-back portions 13 of the stretchable leg cuffs 12 from the side flaps 10 can include other members. Rigidifying means, for example, may be provided in the stretchable leg cuffs 12 or thereof. The rigidifying means must be rigid enough to space the ends of the folded-back portions 13 from the side flaps 10. Suitable materials of the rigidifying means are foams, nonwoven fabric, polyethylene film, foamed film, spray adhesive, foamed elastomer, polyester, polyurethane and high loft materials.

Elastic bodies 30 provided on the side flaps 10 are two natural rubber strips 31, 31 of a 0.18 mm ×1.5 mm sectional area as are the elastic members 14. The strips may be elastomer film, polyurethane film, Lycra, elastic foam or foamed elastic scrum. The natural rubber strips 31 are secured to the backsheet 9 extended widthwise from the topsheet 7 of the side flaps 10 by elastic attachment means 32. The elastic attachment means 32 is flexible and has adhesion which retains the natural rubber strips 31 extended. The elastic attachment means 32 are, e.g., adhesive beads of a hot melt adhesive. Preferably the strips 31 of the elastic bodies 30 have a length substantially equal to that of the elastic members 14 and are arranged side by side with the elastic members 14.

The elastic bodies 30 are secured to the backsheet 9 by ultrasonic bonding or pressure sensitive/heat seal, or simply by an adhesive. In the preferred embodiment, the natural rubber strips 31 and the elastic attachment means 32 are adhesive strips extended in a 0.0013 mm-thickness.

The stand-up barrier cuffs 11 have folded-back portions 20 which are bent inward. A single or a plurality of spacing elastic members 21 (2 in FIG. 2) are arranged in the folded-back portions 20. The stand-up barrier cuffs 11 defined channels 22 with the topsheet 7 along the stand-up barrier cuffs. The channels collect body exudates in the diaper 1 and retain the same. That is, the folded-back portions 20 of the stand-up barrier cuffs 11 have shrinkability sufficient to space the ends of the folded-back portions 20 from the topsheet 7. The stand-up barrier cuff 11 are made of polypropylene, polyester, rayon, nylon, foam, plastic film, formed film, elastic film or others. The stand-up barrier cuffs 11 can be formed by various techniques. For example, the stand-up barrier cuffs 11 can be made of woven fabric, non-woven fabric, spun bonded web, carded web or similar webs. More preferably the stand-up cuffs 11 are formed of polypropylene which has no finished surfaces so as to be impervious to liquids. In the preferred embodiment, the stand-up barrier cuffs 11 are formed of the same members or material as the stretchable leg cuffs 12.

Figure 5:
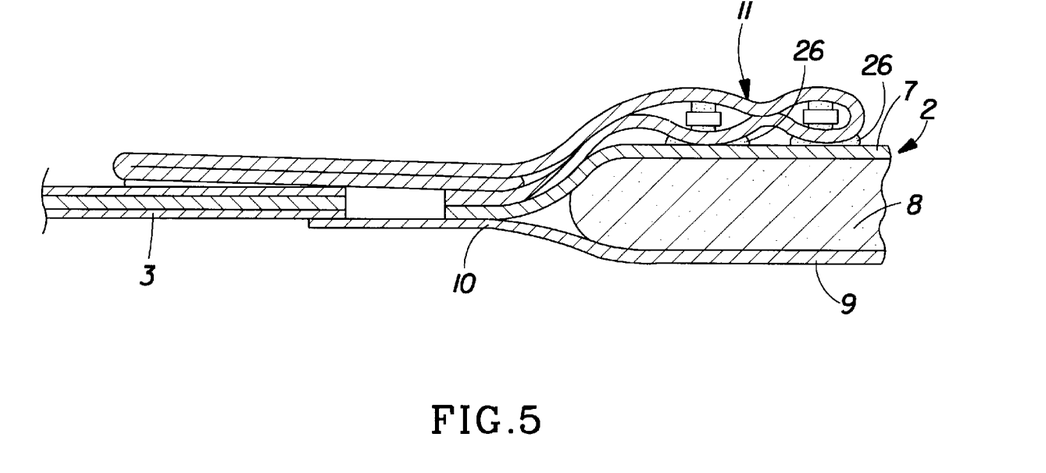
FIG. 5 is a sectional view along the line 5—5 in FIG. 2.

As shown in FIGS. 3 to 5, the stand-up barrier cuffs 11 are so positioned that the forward ends 24 of the inner portion 23 of the folded-back portions 20 are laid below the inner portions 13a of the folded-back portions 13 of the stretchable leg cuffs 12. The forward ends 24 of the inner portions 23 of the folded-back portions 20 are bonded to the top of the topsheet 7 of the side flaps 10. Body exudates, especially faces which cannot be easily absorbed and tend to float along the topsheet 7, contact the channels 22 of the stand-up barrier cuffs 11 before the faces contact the stand-up barrier cuffs 11. The stand-up barrier cuffs 11 and the stretchable leg cuffs 12 constitute effective double constraining means for flow of body exudates.

The ends of the folded-back portions 20 of the stand-up barrier cuffs 11, and the forward ends 24 of the inner portion 23 are spaced from each other to limit an effective width of the stand-up barrier cuffs 11. The ends of the folded-back portions of the stand-up barrier cuffs 11 are parallel or unparallel with each other, linear or curved. As shown in FIGS. 2 to 4, the stand-up barrier cuffs 11 can have circular, square, rectangular or other optional sectional shape. Preferably the ends of the folded-back portions and the ends of the inner portion are linear and parallel with each other so that the stand-up barrier cuffs 11 have a uniform effective width.

It is preferred that the folded-back portions 20 of the stand-up barrier cuffs 11 are spaced from the topsheet 7 at least at the crotch portion 2b of the diaper 1. As the stand-up barrier cuffs 11 define the channels 22 for increase of a diaper capacity, the folded-back portions 20 are preferably spaced from the stopsheet 7.

The stand-up barrier cuffs 11 are preferably hydrophobic, more preferably impervious to liquids for preventing body exudates from passing through. The stand-up barrier cuffs 11 are made liquid impervious by known art, e.g., selective treatments or securing discrete materials. Absorbent means may be provided on the stand-up barrier cuffs 11.

In the preferred embodiment of the diaper 1 shown in FIGS. 3 to 5, the stand-up barrier cuffs 11 are joined to the topsheet 7 of the sideflaps 10 where the backsheet 9 is wider than the topsheet 7. "Meaning of Joined" here covers a case where the stand-up barrier cuffs 11 are separate members directly or indirectly attached to the side flaps, and a case that the stand-up barrier cuffs 11 are made of the same member or material as the diaper 1 and has a one-piece structure with the side flaps 10. In the preferred embodiment, the stand-up barrier cuffs 11 and the stretchable cuffs 12 have a one-piece structure with the side flaps 10.

The stand-up barrier cuffs 11 and the side flaps 10 may be joined to each other by securing parts of the stand-up barrier cuffs 11 directly to the backsheet 9, or securing the stand-up barrier cuffs 11 to an intermediate member and securing the intermediate member to the backsheet 9. In the preferred embodiment, the stand-up barrier cuffs 11 and the side flaps 10 are joined directly to each other by an adhesive, or other arbitrary attachment means, e.g., heat/press seal, ultrasonic wave bonding, or known art. Preferably this seal means is the same as the seal means for joining the stretchable leg cuffs 12 to the side flaps 10.

The seal means which joins the inner portions of the folded-back portions of the stand-up barrier cuffs 11 to the side flaps 10 form leakage-resistant seals which are barriers to liquid penetration through the topsheet 7 for preventing liquid from penetrating into the edge of the diaper from below the stand-up barrier cuffs 11.

A single or a plurality of spacing elastic members 21 provided in the folded-back portions 20 of the stand-up barrier cuffs 11 are optional means which gathers, shrinks and shortens, or stands the stand-up barrier cuffs 11 to define channels 22 which function a barrier for leakage of body exudates. The spacing elastic members 21 are secured tot he stand-up barrier cuffs 11 elastically extended and, in their normal non-constrained state, shrink or gather the folded-back portions 20 of the stand-up barrier cuffs 11.

The spacing elastic members 21 depend on a general design of the diaper. In the preferred embodiment of FIG. 2, the spacing elastic members 21 are extended along substantially entire lengths of the stand-up barrier cuffs 11 in the crotch portion 2b. In the most preferred embodiment, the spacing elastic members 21 are extended beyond the crotch portion 2b to the vicinity of the end edge of the diaper, most effectively spacing the stand-up barrier cuffs 11 from the topsheet 7. As shown in FIG. 3, the spacing elastic members 21 are secured to the inside of the folded-back portion 20 by spacing elastic member attachment means 25, 25. Most preferably the spacing elastic members 21 are elastic strands of natural rubber of a 0.18 mm×1.5 mm sectional area. The spacing elastic members 21 may be an arbitrary known thermal shrinkable elastic material. Other suitable elastic materials are, e.g., elastomer film, polyurethane film, elastomer foam. In the preferred embodiment, the spacing elastic members 21 and the elastic attachment means 25 are extensible adhesive strips of a 0.5 mm thickness.

The preferred spacing elastic members 21 for spacing the ends of the folded-back portion of the stand-up barrier cuffs 11 from the stopsheet 7 may include some kinds of other elements as described in connection with the spacing means for the stretchable leg cuffs 12.

Closure means 26 (FIG. 5) for securing the folded-back portions 20 of the barrier cuffs 11 to the stopsheet 7 give a wearer comfortable fit and prohibit the folded-back portions 20 from reversing while being worn and used. "Reversing" here means that the folded-back portions 20 folded inside are turned outside while being worn. The closure means 26 is, e.g., a hot melt adhesive, and may be known art, such as ultrasonic bonding, heat/pressure sealing or others.

The side panels 3 are for improving comfortableness of disposable garments. The side panels 3 are first conformed to a contour for good fit, and expand or diminish the side surfaces of the garments to retain the good fit.

The side panels 3 are extended generally from the side edges of the ends of the side flaps 10 to the leg edges forming the leg openings. As shown in FIG. 2, the backsheet 9 has a rectangular shape having opposed side edges 50 and opposed side edges 51. The side panels 3 in a substantially trapezoidal shape are extended from both side edges 50 outward near the front part 2a and the rear part 2c. The side panels 3 have required widthwise elastically extensibility. "Elastically extensibility" here means being extensible at least in one direction (preferably widthwise) when a tensile force (widthwise tensile force) is applied and being able to return to its original size and shape when the tensile force is removed.

The side seams 6 are formed by joining the side edges of the front part 2a and of the rear part 2c positioned on the same side to each other. The side seams 6 are formed by joining the parts of the side panels 3 projecting outside the side surface areas of the side panels 3 in fin seams projected to the sides by known joint forming means. The side seams 6 my be formed by ultrasonic bonding, heat sealing, adhesive bonding.

Figure 6:
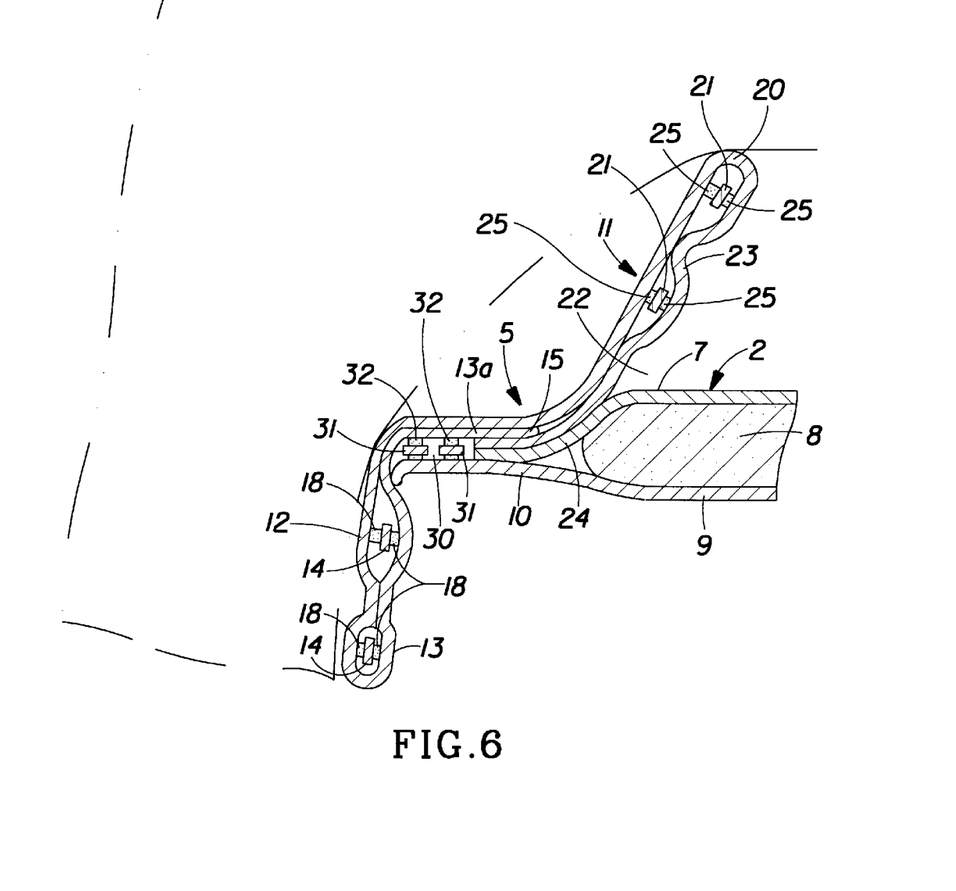
FIG. 6 is view of the disposable pull-on diaper of FIG. 1.

When the pull-on diaper 1 is put on, the legs of a wearer are passed from above through the leg openings 4 of the pull-on diaper 1, and then the pull-on diaper 1 is slid upward along the legs to a required position. As shown in FIG. 6, the elastic bodies 30 provided in the side flaps 10 elastically fit parts of the legs of the wearer near the crotch with the stretchable leg cuffs 12 positioned outer than the elastic bodies 30 elastically fit the legs lower of the elastic bodies 30. Thus the pull-on diaper 1 fits each leg of the wearer at two points near the associated leg opening 4 of the pull-on diaper 1. Thus, the stretchable leg cuffs 12 are arranged around the legs of the wearer with little gap around the legs. Elastic leg openings of a sufficient width are provided but with gasket action around the leg openings improved, while liquid leakage can be prevented around the legs.

By thus elastically fitting the legs of a wearer the elastic leg cuffs 12 are hindered from being folded inside, and even when body exudates are held by the absorbent body 2, the absorbent body 2 is retained at the crotch of the wearer without hanging down.

Because the side panels 3 are attached to the side flaps 10 as shown in FIG. 2, a width X of the side panels 3 can be set independently of a width of the stretchable elastic leg cuffs 12. Sufficient dynamic fit can be secured around the waist.

What is claimed is:

1. An absorbent product with leg closures comprising:
    an absorbent body including an absorbent core positioned between a topsheet having an extended portion and a backsheet having an extended portion;
    a pair of side flaps having side edges and extending widthwise from the absorbent core, said side flaps being formed from said extended portions of said backsheet and said topsheet, elastic bodies being arranged within each said side flap thereby elasticizing each said side flap;
    a pair of stretchable side panels extending outwardly from said side edges of said side flaps;
    stand-up barrier cuffs being positioned on said side flaps along a length of the absorbent body; and
    stretchable leg cuffs being attached to said barrier cuffs and extending further outward from said absorbent body and being positioned onto said side flaps along the lengths of the side flaps for enclosing the legs of said barrier cuffs and said stretchable leg cuffs about a wearer.

2. The absorbent product with leg closures according to claim 1, wherein the absorbent product is a diaper.

3. The absorbent product with leg closures according to claim 2, wherein a width extended further outward is 2.5–50 mm for children and 4–90 mm for adults.

4. The absorbent product with leg closures according to claim 1, wherein the stretchable leg cuffs are formed of a liquid impervious material.

* * * * *